United States Patent [19]

Nakamura et al.

[11] Patent Number: 4,590,227
[45] Date of Patent: May 20, 1986

[54] WATER-SWELLABLE ELASTOMER COMPOSITION

[75] Inventors: Morio Nakamura, Kakogawa; Shigeji Obayashi, Akashi; Shinichi Takemori, Takasago; Hitoshi Tanaka; Motomu Hirakawa, both of Kakogawa, all of Japan

[73] Assignee: Seitetsu Kagaku Co., Ltd., Hyogo, Japan

[21] Appl. No.: 664,175

[22] Filed: Oct. 24, 1984

[51] Int. Cl.$^4$ .......................... C08L 1/26; C08L 3/04; C08L 7/00; C08L 9/00
[52] U.S. Cl. ..................... 523/130; 524/43; 524/44; 524/45; 525/54.3; 525/54.31; 525/54.32; 525/57; 525/199; 525/215; 525/232
[58] Field of Search ............... 525/215, 227, 232, 404, 525/57, 54.3, 54.31, 54.32, 199; 523/130; 524/43, 44, 45

[56] References Cited

U.S. PATENT DOCUMENTS

| 3,956,224 | 5/1976 | Chu | 525/404 |
| 4,174,309 | 11/1979 | Stournas | 523/130 |
| 4,277,582 | 7/1981 | Mueller et al. | 525/404 |
| 4,367,297 | 1/1983 | Hübner et al. | 523/130 |
| 4,476,276 | 10/1984 | Gasper | 523/130 |

FOREIGN PATENT DOCUMENTS

| 2847342 | 5/1979 | Fed. Rep. of Germany | 525/404 |
| 56-33032 | 3/1981 | Japan . | |
| 57-190065 | 11/1982 | Japan . | |

*Primary Examiner*—Allan M. Lieberman
*Attorney, Agent, or Firm*—Pollock, Vande Sande & Priddy

[57] ABSTRACT

Water-swellable elastomer composition consisting essentially of a homogeneous mixture of an elastomer, a water-absorbent resin and a water-soluble resin. Said composition exhibits a high degree of swelling and a high swelling rate when it is soaked in water. Also, said composition retains swellability even when it is put in contact with water for a long period of time.

15 Claims, No Drawings

WATER-SWELLABLE ELASTOMER COMPOSITION

This invention relates to a water-swellable elastomer composition consisting essentially of an elastomer, a water absobent resin and a water-soluble resin.

Heretofore, there has been proposed the use of a water-swellable rubber which is produced by mixing a rubber with a water-absorbent material such as crosslinked polyvinyl alcohol, crosslinked polyacrylate, crosslinked starch-acrylate copolymer, crosslinked carboxymethylcellulose or the like; a water-swellable urethane resin; a hydrophilic group-containing rubber; or the like for the purpose of the caulking or sealing of gaps or the stopping of water in civil engineering and construction works or the like, or the preservation of airtightness in machinary and apparatus [Japanese Patent Application Kokai (Laid-Open) Nos. 33,032/81 and 190,065/82].

However, if water-swellability is imparted to a rubber by mixing a water-absorbent material therewith, the swelling rate and degree of swelling of the rubber are low, and in addition, the rubber has also such problems as the separation of the water-absorbent material upon contacting with water for a long period of time, so that the swellability is ultimately lost, the strength is remarkably decreased, and the water is polluted.

When a water-swellable urethane resin or hydrophilic group-containing rubber is mixed with a rubber, the water-swellability of the rubber thus obtained is inferior because these have a low degree of swelling and a low swelling rate, and therefore, no satisfactory effect can be expected.

The present inventors have conducted extensive research for the purpose of overcoming the above-mentioned problems. As a result thereof, they have found that when a water-absorbent resin and a water-soluble resin are homogeneously dispersed in an elastomer, separation of the water-absorbent resin can be prevented, and a water-swelling elastomer composition having an extremely high swelling rate and an extremely high degree of swelling is obtained.

An object of this invention is to provide an elastomer which can be swollen with water.

Another object of this invention is to provide a water-swellable elastomer composition having an extremely high swelling rate and a high degree of swelling.

Other objects and advantages of this invention will be apparent from the following description.

According to this invention, there is provided a water-swellable elastomer composition having a high swelling rate and a high degree of swelling, said composition consisting essentially of a homogeneous mixture of the following three components: an elastomer, a water-absorbent resin and a water-soluble resin.

The elastomer used in this invention includes natural rubbers and synthetic rubbers. The synthetic rubber includes many known rubbers such as chloroprene rubber, butadiene rubber, styrene-butadien rubber, acrylonitrile-butadiene rubber, isobutylene-isoprene rubber, fluororubber, ethylene-propylene rubber, chloro-sulfonated polyethylene, silicone rubber, urethane rubber, polysulfide rubber, acrylic rubber and the like, and it is preferable to use chloroprene rubber or styrene-butadiene rubber from the standpoint of processability and economy.

These rubbers can be properly selected depending upon the application fields of water-swellable rubbers. For instance, chloroprene rubber or chlorosulfonated polyethylene are suitable for the requirement of weather resistance, and silicone rubber or fluororubber are preferred when heat resistance is required.

The water-absorbent resin used in this invention includes crosslinked products of polyacrylates, crosslinked products of starch-acrylate graft copolymers, crosslinked products of a hydrolyzate of starch-acrylonitrile graft copolymer, crosslinked products of carboxymethylcellulose, crosslinked products of polyvinyl alcohol, crosslinked products of a hydrolyzate of methyl (meth)acrylate-vinyl acetate copolymer, crosslinked products of cellulose-sodium acrylate graft copolymer, and the like, and in particular, crosslinked products of polyacrylates have an excellent effect.

Although any of the above water-absorbent resins can be used in this invention, it is necessary to use a water-absorbent resin which absorbs water in an amount of at least 20 times the weight of the resin.

The water-soluble resin used in this invention includes polyethylene oxide, polyvinyl pyrrolidone, hydroxyethylcellulose, hydroxypropylcellulose or the like. Polyethylene oxide and polyvinyl pyrrolidone are preferably used from the standpoint of rubber-compatibility and processability because they are thermoplastic, and a water-swellable elastomer containing polyethylene oxide or polyvinyl pyrrolidone is preferred in view of the appearance and performance.

The amount of the water-absorbent resin added is 5–300 parts by weight, preferably 10–200 parts by weight, per 100 parts by weight of the elastomer. If the content of the water-absorbent resin is too small, neigher satisfactory swelling rate nor satisfactory degree of swelling are obtained. On the other hand, if the content is too large, the water-absorbent resin is separated from the elastomer, and the composition becomes in some cases unsuitable for water stopping or water retention.

A water-swellable elastomer obtained by mixing an elastomer only with a water-absorbent resin as is usual in the conventional method exhibits only slow swelling rate and a low degree of swelling. Moreover, the water-absorbent resin is separated from the water-swellable elastomer in some cases, and hence, the purpose is not achieved.

However, by adding a water-soluble resin together with a water-absorbent resin to an elastomer according to this invention, a homogeneous water-swelling elastomer composition is obtained, and when it contacts with water a swollen product which has a high degree of swelling, is homogeneous and has a smooth surface, is obtained from the water-swelling elastomer composition.

The amount of the water-soluble resin added is 0.5–100 parts by weight, preferably 1–50 parts by weight, per 100 parts of the elastomer. If the amount of the water-soluble resin is too small, the intended effect of the addition cannot be obtained and the degree of swelling of the elastomer is low. If the amount of the water-soluble resin is too large, the degree of swelling is not so much increased, and adverse effects such as elution or the like tend to take place.

The particle diameter of a water-absorbent resin used in this invention is 400 $\mu$m or less, preferably 100 $\mu$m or less. If the particle becomes finer, a more homogeneous composition is obtained, and a swollen product obtained therefrom becomes homogeneous.

When 10-100 parts by weight of water per 100 parts by weight of the water-absorbent resin is previously contained in an elastomer prior to mixing the elastomer with the water-absorbent resin, a water-swelling elastomer composition having an extremely high swelling rate is obtained. If the amount of water is too small, the effect is not sufficient. On the other hand, if the amount of water is too large, mixing operation becomes difficult. As for the stage of enabling water to be contained it is not always necessary to previously contain the water in the water-absorbent resin, and an equivalent effect is obtained by adding water at the time of mixing.

The water-swellable elastomer of this invention is produced by uniformly dispersing a water-absorbent resin and a water-soluble resin in an elastomer by a mechanical procedure. For example, roll mixing, mixing with a Banbury mixer, mixing with an extruder, or the like are mechanical dispersing methods which are applicable to this invention. A vulcanizing agent and a vulcanization accelerator are mixed during the mixing procedure in this invention, and if necessary, a coloring agent, a filler, a plasticizer, an antioxidant and the like are incorporated. The compound obtained by mixing is heat-vulcanized and molded according to a conventional method to form a water-swellable elastomer composition in the form of a plate, rod or the like depending on intended uses.

The water-swellable elastomer of this invention can be applied to various uses such as water-stopping material, water-retaining material, medical supplies and the like, and suitable compounding recipes are selected depending upon uses to form compositions.

This invention is further explained in detail below referring to Examples and Comparative Examples. However, it should not be interpreted that this invention be limited to the Examples.

Degree of swelling in the Examples and Comparative Examples is defined as follows:

$$\text{Degree of swelling} = \frac{b - a}{a} \times 100 \, (\%)$$

a: weight before swelling,
b: weight after swelling.

The size of a sample is 2×4 cm with a thickness of 1 mm.

In the Examples and Comparative Examples all parts are by weight unless otherwise specified.

EXAMPLE 1

A compound obtained by roll-mixing a chloroprene rubber (Toyo Soda Mfg. Co., Ltd.: Skyprene B-30) as an elastomer, a crosslinked product of polysodium acrylate (Seitetu Kagaku Co., Ltd.: Aquakeep 4S, average particle diameter, 70μ) as a water-absorbent resin and a polyethylene oxide (Seitetsu Kagaku Co., Ltd.: PEO-3) as a water-soluble resin in the amounts shown in Table 1 was vulcanized at 150° C. at a pressure of 150 kg/cm² G for 30 minutes to prepare a water-swellable elastomer composition. A sheet of 20×40×1 mm was formed from this elastomer composition, and soaked in ion-exchanged water to swell the sheet.

The degrees of swelling are shown in Table 2.

TABLE 1

| Component | Part |
| --- | --- |
| Chloroprene | 100 |
| Carbon black | 30 |
| Zinc white | 5 |
| Magnesium oxide | 4 |
| Stearic acid | 1 |
| Ethylene thiourea | 0.5 |
| Aquakeep 4S | 100 |
| Polyethylene oxide | 10 |

TABLE 2

| Soaking Time | 10 min | 1 hr | 24 hrs |
| --- | --- | --- | --- |
| Degree of swelling (%) | 40 | 98 | 830 |

EXAMPLE 2

A compound obtained by roll-mixing a styrenebutadiene rubber (Sumitomo Chemical Co., Ltd.: Sumitomo SBR 1778S) as an elastomer, a crosslinked product of polysodium acrylate (Seitetsu Kagaku Co., Ltd.: Aquakeep 4S, average particle diameter, 70 μm) as a water-absorbent resin and a polyethylene oxide (Seitetsu Kagaku Co., Ltd.: PEO-3) as a water-soluble resin in the amounts shown in Table 3 was vulcanized at 150° C. at a pressure of 150 kg/cm² G for 30 minutes to produce a water-swellable elastomer composition. The degree of swelling determined in the same manner as in Example 1 are shown in Table 4.

TABLE 3

| Component | Part |
| --- | --- |
| Styrene-butadiene rubber | 100 |
| Carbon black | 30 |
| Sulfur | 4 |
| 2-Benzothiazyl disulfide | 2 |
| Tetramethylthiuram disulfide | 1 |
| Aquakeep 4S | 100 |
| Polyethylene oxide | 10 |
| Water | 30 |

TABLE 4

| Soaking Time | 10 min | 1 hr | 24 hrs |
| --- | --- | --- | --- |
| Degree of swelling (%) | 75 | 240 | 1,570 |

COMPARATIVE EXAMPLE 1

A water-swellable elastomer composition was prepared in the same manner as in Example 1, except that the polyethylene oxide was omitted. Because of the absence of polyethylene oxide, the components were unable to be homogeneously mixed, and the water-absorbent resin was remarkably separated off from the elastomer 2 hours after the soaking in water.

COMPARATIVE EXAMPLE 2

A water-swelling elastomer composition was prepared in the same manner as in Example 2, except that the polyethylene oxide was omitted. The degrees of swelling determined in the same manner as in Example 1 are shown in Table 5.

TABLE 5

| Soaking Time | 10 min | 1 hr | 24 hrs |
| --- | --- | --- | --- |
| Degree of | 18 | 45 | 315 |

EXAMPLE 3

A water-swellable elastomer composition was prepared in the same manner as in Example 2, except that a crosslinked product of starch-acrylate graft copolymer (Sanyo Chemical Industry, Ltd.: Sanwet IM-300) was used as a water-absorbent resin instead of the crosslinked product of polysodium acrylate. The degrees of swelling determined in the same manner as in Example 1 are shown in Table 6.

TABLE 6

| Soaking Time | 10 min | 1 hr | 24 hrs |
|---|---|---|---|
| Degree of swelling (%) | 50 | 170 | 1,150 |

EXAMPLE 4

A water-swellable elastomer composition was prepared in the same manner as in Example 2, except that a hydroxyethylcellulose (FUJI CHEMICAL CO., LTD.: Fujihec AH-15) was substituted for the polyethylene oxide. The degrees of swelling determined in the same manner as in Example 1 are shown in Table 7.

TABLE 7

| Soaking Time | 10 min | 1 hr | 24 hrs |
|---|---|---|---|
| Degree of swelling (%) | 40 | 150 | 1,050 |

EXAMPLE 5

A water-swellable elastomer composition was prepared in the same manner as in Example 2, except that a polyvinylpyrrolidone (KISHIDA KAGAKU: K-15) was substituted for the polyethylene oxide.

Soaking the sheet obtained in water for a predetermined time and observing the surface state, the swollen product was found to be smooth and slimeless. The degrees of swelling determined in the same manner as in Example 1 are shown in Table 8.

TABLE 8

| Soaking Time | 10 min | 1 hr | 24 hrs |
|---|---|---|---|
| Degree of swelling (%) | 60 | 210 | 1,250 |

EXAMPLES 6-10

A water-swellable elastomer composition was prepared by vulcanizing at a pressure of 150 kg/cm² G at 150° C. for 30 minutes a compound obtained by roll-mixing the components shown in Table 9 in the same manner as in Example 1. The degrees of swelling determined in the same manner as in Example 1 are shown in Table 10. The swollen sheets had favorable surfaces which were smooth and slimeless.

TABLE 9

| Example No. | 6 | 7 | 8 | 9 | 10 |
|---|---|---|---|---|---|
| EPT | 100 | | | | |
| NR | | 100 | | | |
| CSM | | | 100 | | |
| NBR | | | | 100 | |
| IIR | | | | | 100 |
| Carbon black | 30 | 30 | 30 | 30 | 30 |
| Zinc white (ZnO) | 3 | 3 | | 5 | 5 |
| Magnesium oxide (MgO) | | | 5 | | |
| Sulfur (S) | 1.5 | 2 | | 1.5 | |
| Stearic acid | 1 | 1 | 1 | 1 | 1 |
| Vulcanization accelerator M | 0.5 | | | | |
| Vulcanization accelerator TT | 1.0 | | | 0.5 | |
| Vulcanization accelerator BZ | | | | | 1 |
| Vulcanization accelerator TRA | | 2 | | | |
| Vulcanization accelerator DM | | 0.5 | | | |
| Vulcanization accelerator PZ | | 1 | | | |
| Antioxidant (Antigen NBC) | | | 1 | | |
| Process oil | 10 | 10 | 10 | 10 | 10 |
| AK-4S | 70 | | | 70 | |
| Waterlock A-100 | | 70 | | | |
| Sumikagel S-50 | | | | 70 | |
| Water | 35 | 35 | 35 | 35 | 35 |
| PVP | 15 | 15 | 15 | 15 | 15 |

Note:

| Symbol | Compound | Trade Name | Manufacturer |
|---|---|---|---|
| EPT: | Ethylene-propylene terpolymer rubber | Esprene 505 | Sumitomo Chem. |
| NR: | Natural rubber | — | — |
| CSM: | Chlorosulfonated polyethylene rubber | Hypalone 40 | Dupont |
| NBR: | Nitrile rubber | Nipole 1042 | Nippon Zeon |
| IIR: | Isobutylene-isoprene rubber | ESSO-BUTYL 268 | Esso. Chem. |
| M: | 2-Mercaptobenzothiazole | | |
| TT: | Tetramethylthiuram disulfide | | |
| BZ: | Zinc dibutyldithiocarbamate | | |
| TRA: | Dipentamethylenethiuraum tetrasulfide | | |
| DM: | Dibenzothiazyl disulfide | | |
| PZ: | Zinc dimethyldithiocarbamate | | |
| Antioxidant | Nickel dibutyldithiocarbamate | Antigen NBC | Sumitomo Chem. |
| AK-4S: | Crosslinked product of polysodium acrylate | Aquakeep 4S | Seitetsu Kagaku |
| Waterlock -A100: | Crosslinked saponification product of startch-acrylonitrile copolymer | Grain-processing Corp. | |
| Sumikagel S-50: | Crosslinked saponification product of methyl acrylate-vinyl acetate copolymer | Sumitomo Chem. | |
| PVP: | Polyvinylpyrrolidone | K-15 | KISHIDA KAGAKU |

TABLE 10

| Soaking Time | 10 min | 1 hr | 24 hrs |
|---|---|---|---|
| Example 6 | 30 | 70 | 580 |
| Example 7 | 25 | 65 | 520 |
| Example 8 | 30 | 70 | 600 |
| Example 9 | 20 | 60 | 500 |
| Example 10 | 30 | 75 | 530 |

What is claimed is:

1. A water-swellable elastomer composition consisting essentially of a homogeneous mixture of an elastomer 5–300 parts by weight of a water-absorbent resin per 100 parts by weight of the elastomer and wherein said water-absorbent resin absorbs water in an amount of at least 20 times the weight of the resin and has particle size of 400 μm or less, and 1–50 parts by weight of a water-soluble resin per 100 parts by weight of the elastomer.

2. The composition of claim 1 wherein the particle size of said water-soluble resin is 100 μm or less.

3. A composition according to claim 1, wherein the amounts of the water-absorbent resin and the water-soluble resin are, respectively, 10–200 parts by weight and 1–50 parts by weight per 100 parts by weight of the elastomer.

4. A composition according to claim 1, wherein the elastomer is a chloroprene rubber, a butadiene rubber, a styrene-butadiene rubber, an acrylonitrile-butadiene rubber, an isobutylene-isoprene rubber, a fluororubber, an ethylene-propylene rubber, a chlorosulfonated polyethylene, a silicone rubber, an urethane rubber, a polysulfide rubber, an acrylic rubber or a natural rubber.

5. A composition according to claim 1, wherein the elastomer is a chloroprene rubber.

6. A composition according to claim 1, wherein the elastomer is a styrene-butadiene rubber.

7. A composition according to claim 1, wherein the water-absorbent resin is a crosslinked product of polyacrylate, a crosslinked product of starch-acrylate graft copolymer, a crosslinked product of hydrolyzate of startch-acrylonitrile graft copolymer, a crosslinked product of carboxymethylcellulose, a crosslinked product of polyvinyl alcohol, a crosslinked product of hydrolyzate of methyl (meth)acrylate-vinyl acetate copolymer or a crosslinked product of cellulose-sodium acrylate graft copolymer.

8. A composition according to claim 1, wherein the water-absorbent resin is a crosslinked product of polyacrylate.

9. A composition according to claim 1, wherein the water-absorbent resin is a crosslinked product of starch-acrylate graft copolymer.

10. A composition according to claim 1, wherein the water-soluble resin is a polyethylene oxide, a polyvinylpyrrolidone, a hydroxyethylcellulose or a hydroxypropylcellulose.

11. A composition according to claim 1, wherein the water-soluble resin is a polyethylene oxide.

12. A composition according to claim 1, wherein the water-soluble resin is a polyvinyl pyrrolidone.

13. A composition according to claim 1, wherein the water-absorbent resin is in the form of a powder having a particle diameter of 100 μm or less.

14. A composition according to claim 1, wherein the water-absorbent resin and the water-soluble resin are homogeneously dispersed in the elastomer.

15. A composition according to claim 1, wherein the water-absorbent resin is a water-absorbent resin having previously absorbed therein 10–100 parts by weight of water per 100 parts by weight of the water-absorbent resin.

* * * * *

UNITED STATES PATENT AND TRADEMARK OFFICE
CERTIFICATE OF CORRECTION

PATENT NO. : 4,590,227
DATED : May 20, 1986
INVENTOR(S) : Nakamura, et al.

It is certified that error appears in the above—identified patent and that said Letters Patent is hereby corrected as shown below:

Column 7, line 11, change "soluble" to -- absorbent --.

Signed and Sealed this

Twenty-fifth Day of November, 1986

*Attest:*

DONALD J. QUIGG

*Attesting Officer*      *Commissioner of Patents and Trademarks*